United States Patent [19]

Berge

[11] 4,247,306
[45] Jan. 27, 1981

[54] DETECTION OF FLAWS IN METAL MEMBERS

[75] Inventor: Arnulf Berge, Vågsbygd, Norway

[73] Assignee: Elkem Spigerverket A/S, Oslo, Norway

[21] Appl. No.: 1,460

[22] Filed: Jan. 17, 1979

Related U.S. Application Data

[63] Continuation-in-part of Ser. No. 957,343, Nov. 3, 1978, abandoned.

[51] Int. Cl.³ ............................................. B24B 1/00
[52] U.S. Cl. .................................. 51/322; 51/165.72; 51/165.73; 73/15 FD
[58] Field of Search ............. 73/15 FD; 51/34 R, 35, 51/165.71, 165.72, 165.73, 165.74, 165.91

[56] References Cited

U.S. PATENT DOCUMENTS

| | | | |
|---|---|---|---|
| 1,869,336 | 7/1932 | DeForest | 73/15 |
| 2,845,755 | 8/1958 | Price | 51/165.91 |
| 3,020,745 | 2/1962 | Sielicki | 73/15 |
| 3,206,603 | 9/1965 | Mauro | 73/15 |
| 3,566,669 | 3/1971 | Lawrence et al. | 73/15 |
| 3,898,440 | 8/1975 | Fukuma et al. | 51/165.71 |
| 3,953,943 | 5/1976 | Nakaoka | 51/165.74 |
| 3,992,826 | 11/1976 | Nakaoka | 51/35 |
| 4,109,508 | 8/1978 | Fukuyama | 73/15 |

OTHER PUBLICATIONS

"Thermal and Infrared Nondestructive Green Testing of Composites & Ceramics" in Materials et al.

Primary Examiner—Herbert Goldstein
Attorney, Agent, or Firm—Eyre, Mann, Lucas & Just

[57] ABSTRACT

A method of detecting flaws in metal members is disclosed. The metal member is exposed to high frequency heating whereupon the temperature profile across the work piece is measured, preferably by recording with an infrared camera. The recorded data can be used for automatic marking or repair of the metal member.

1 Claim, 1 Drawing Figure

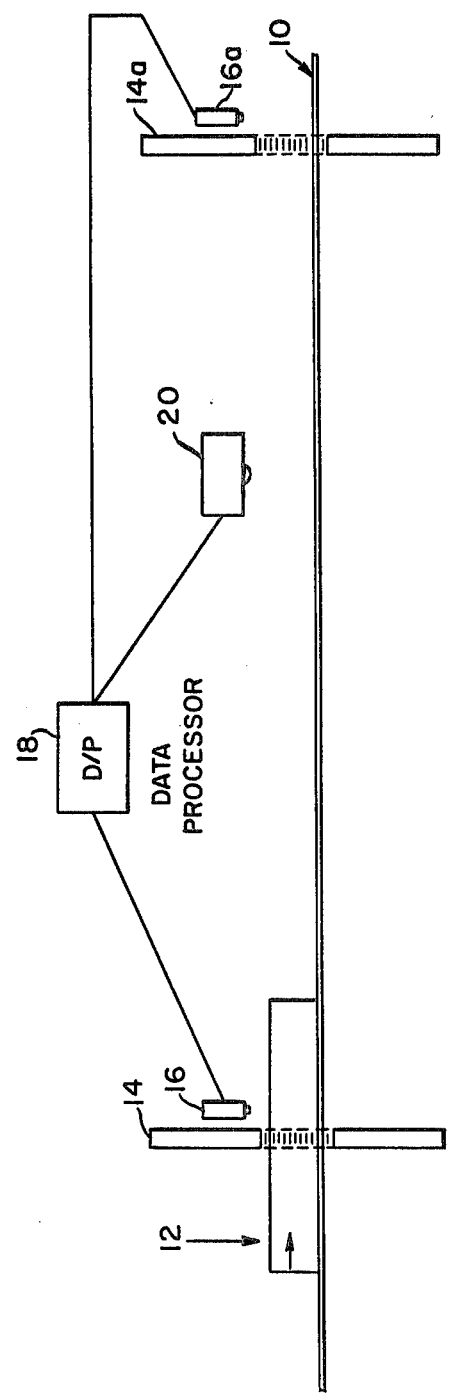

DETECTION OF FLAWS IN METAL MEMBERS

The present application is a continuation-in-part of application Ser. No. 957,343, filed Nov. 3, 1978 now abandoned.

The present invention relates to a method for flaw detection for metal members and, in particular, metal blooms or billets such as of steel, aluminum or the like.

It is, of course, well known in the art that surface flaws occur in the formation of steel work pieces such as blooms or billets, and many different attempts have been made to detect these surface flaws for the purpose of eliminating them by grinding or the like. Indeed, many of these methods are in commercial use today and have proved to be quite successful. While successful, they unfortunately also have drawbacks.

One method used for detecting surface flaws involves the use of a magnetic field. Surface flaws are initially filled with air, slag, oxides or the like, as a result of which the surface flaws, and notably cracks, will have a poorer magnetic conductivity than the rest of the work piece. There is thereby obtained a strong magnetic field in a direction transverse to the cracks and this strong magnetic field can be detected to indicate surface flaws.

In yet another known method, a fluorescent magnetic powder is distributed on the surface of the work piece. The powder will tend to collect to a greater degree in the surface flaws which can then be exposed by ultraviolet light. In still another method, the work piece is magnetized by passing a current through it, after which it is covered with a magnetically attractable powder including a coloring agent which will melt and adhere to the billet upon heating. The metal object in then heated to a sufficient intensity to cause the coloring agent to adhere and, because of the stronger magnetic attraction at the cracks, it will show up the most at these locations. This process can be fully automatic and is described in U.S. Pat. No. 3,845,383.

Other methods for detecting surface flaws are also known and, in fact, the art is quite well developed. However, there are disadvantages to all of the known prior art processes. These involve one or more of a combination of the process not being automatic or using up relatively expensive materials, such as the magnetically attractable compositions, or being inaccurate, or requiring the application of a powder, dust or liquid which inherently creates an undesirable environmental condition.

The applicant has now discovered that all of the foregoing disadvantages of prior art processes can be overcome by the relatively simple expedient of employing high frequency heating and measuring the resulting temperature profile of the metal work piece, suitably by recording with an infrared camera. Surface flaws on blooms, billets and the like are characterized by sharp edges and other irregularities in the surface, and these become much hotter than the surrounding areas when subjected to high frequency inductive heating. Because of this great difference in temperature, a temperature profile can be developed which will pinpoint the location of the surface flaws.

Because of the high heat conductivity of metal materials, it is necessary to observe the temperature profile either during the high frequency heating or immediately thereafter, e.g., within no more than about 2-3 seconds. For achieving this result, an infrared camera has been found to be especially desirable. In fact, use of this apparatus permits the process to be made fully automatic, including the marking or subsequent grinding operation.

These and other features of the present invention may be more fully understood with reference to the FIGURE, which shows a schematic of an apparatus which can be used in the present invention.

In the FIGURE is shown a track 10, along which a billet 12 is progressing in the direction of the arrow as indicated thereon. In the picture as shown, the billet passes through an induction heater 14 which operates at high frequency, preferably above about 10,000 hertz. Positioned immediately downstream from the induction heater 14 is an infrared thermo-camera 16 which scans the work piece and forms a temperature profile. When the temperature across the work piece is measured, there will be found an increase in temperature adjacent surface irregularities, such as cracks. The temperature profile will form a streaked temperature pattern across the surface, and the surface irregularities will be indicated by the fact that the streaked pattern repeats itself. The data obtained from the infrared camera can be recorded as a hard copy but is preferably fed directly to a data processor 18, which in turn controls downstream equipment 20, such as a marking pen or grinding equipment. In this way, the detected flaws can be automatically marked or they can be automatically ground out. Since the size, shape and depth of the crack will be discernible from the temperature profile, the exact grinding necessary to remove it can be determined by an appropriate program. Obviously, the treated billet can be subjected again to the flaw detection apparatus 14A, 16A to insure that the correct grinding has been effected and, by appropriate feed back of data to the data processor 18, adjustments in the grinder 20 can be automatically made.

One of the most important advantages of the present invention, in addition to those hereinbefore delineated, is that the method can be used equally well with non-magnetic metal work pieces. This is indeed a great advantage since the magnetic processes are totally unsuitable for use with non-ferrous materials, and these magnetic methods are the most widely used today.

It will be understood that the claims are intended to cover all changes and modifications of the preferred embodiments of the invention, herein chosen for the purpose of illustration, which do not constitute departures from the spirit and scope of the invention.

What is claimed is:

1. A method of detecting surface flaws in a non-magnetic metallic workpiece comprising:
    (a) heating said non-magnetic metallic workpiece by passing said workpiece through an induction heater for induction heating with a high frequency current;
    (b) scanning said non-magnetic metallic workpiece with an infrared camera to determine a temperature profile of the scanned portion of said non-magnetic metallic workpiece within 3 seconds of the time of heating;
    (c) generating an output signal in said first infrared camera corresponding to said temperature profile;
    (d) feeding said output signal to a data processor which controls a grinding apparatus for automatically grinding said workpiece in accordance with said temperature profile;
    (e) reheating said non-magnetic metallic workpiece by passing it through a second induction heater;

(f) scanning said non-magnetic workpiece with a second infrared camera to determine a new temperature profile;

(g) generating a correction signal corresponding to said new temperature profile; and (h) feeding said correction signal to said data processor to automatically adjust the grinding apparatus.

* * * * *